United States Patent [19]
Soloshenko et al.

[11] Patent Number: 6,113,851
[45] Date of Patent: Sep. 5, 2000

[54] APPARATUS AND PROCESS FOR DRY STERILIZATION OF MEDICAL AND DENTAL DEVICES AND MATERIALS

[75] Inventors: Igor A. Soloshenko; Vyacheslav V. Tsiolko; Vladimir A. Khomich, all of Kiev, Ukraine

[73] Assignee: Phygen, Minneoplis, Minn.

[21] Appl. No.: 08/999,859

[22] Filed: Feb. 28, 1997

[30] Foreign Application Priority Data

Mar. 1, 1996 [UA] Ukraine ................................ 96030807

[51] Int. Cl.$^7$ ........................................................ A61L 2/14
[52] U.S. Cl. ............................ 422/22; 422/23; 422/186; 422/305; 250/396 R; 250/423 R; 250/492.1; 250/492.3; 250/493.1; 250/496.1
[58] Field of Search ................................ 422/21–23, 186, 422/305; 250/396 R, 423 R, 492.1, 492.3, 493.1, 496.1

[56] References Cited

U.S. PATENT DOCUMENTS

| | | | |
|---|---|---|---|
| 3,831,052 | 8/1974 | Knechtli | 313/187 |
| 3,948,601 | 4/1976 | Fraser et al. | 21/54 R |
| 4,207,286 | 6/1980 | Gut Baucher | 422/21 |
| 4,348,357 | 9/1982 | Bithell | 422/22 |
| 4,643,876 | 2/1987 | Jacobs et al. | 422/23 |
| 4,818,488 | 4/1989 | Jacob | 422/23 |
| 4,898,715 | 2/1990 | Jacob | 422/186.29 |
| 4,931,261 | 6/1990 | Jacob | 422/292 |
| 5,115,166 | 5/1992 | Campbell et al. | 315/111.21 |
| 5,200,146 | 4/1993 | Goodman | 422/23 |
| 5,326,530 | 7/1994 | Bridges | 422/22 |
| 5,393,490 | 2/1995 | Jacob | 422/22 |
| 5,413,760 | 5/1995 | Campbell et al. | 422/24 |
| 5,451,368 | 9/1995 | Jacob | 422/23 |

FOREIGN PATENT DOCUMENTS

| | | |
|---|---|---|
| 53-35715 | 4/1978 | Japan . |
| 60-58662 | 4/1978 | Japan . |

OTHER PUBLICATIONS

Rutala, W.A., and Weber, D.J., "Low Temperature Sterilization Technologies: Do We Need to Redefine Sterilization"?, Infection Control and Hospital Epidemiology, Feb., 1996, pp. 87–91.

Alfa, M.J., et al., "Comparison of Ion Plasma, Vaporized Hydrogen Peroxide, and 100% Ethylene Oxide Sterilizers to the Dec. 1988 Ethylene Oxide Gas Sterilizer," Infection Control and Hospital Epidemiology, Feb., 1996, pp. 92–100.

Primary Examiner—Robert J. Warden, Sr.
Assistant Examiner—Fariborz Moazzam
Attorney, Agent, or Firm—Shanks & Herbert

[57] ABSTRACT

An apparatus and process for accomplishing low-temperature sterilization in a plasma generated using a variety of gas molecules. The plasma is generated using a hollow cathode discharge device of design that permits the device to be of commercially practical size and provides for the generation of moderate but extremely consistent plasma density throughout the chamber, thereby assuring sterilization of all items placed therein.

21 Claims, 4 Drawing Sheets

APPARATUS AND PROCESS FOR DRY STERILIZATION OF MEDICAL AND DENTAL DEVICES AND MATERIALS

BACKGROUND OF THE INVENTION

This invention relates to an improved method for plasma sterilization, the practice of exposing articles to be sterilized to a gas discharge plasma and in so doing sterilizing medical and dental instruments for re-use.

Modern medical and dental practice involves the use and re-use of certain instruments which cannot withstand the high temperatures and steam pressures historically used to sterilize instruments. Such autoclave sterilization worked, and continues to work, for stainless steel and metal instruments. Newer instruments requiring re-use which cannot be sterilized using an autoclave without damage are fiber-optic devices, e.g., angioscopes, bronchioscopes, endoscopes, and proctoscopes—ductile plastic devices, metal products which corrode, rubber gloves, gowns, sutures, syringes, and catheters.

One sterilization technique used for such temperature sensitive devices involves exposure of the articles to pressurized ethylene oxide ($C_2H_4O$) in a leak-proof, shatter-proof container. The ethylene oxide must permeate the entire article for effective sterilization. Articles must be exposed to these conditions for up to three hours to achieve the desired level of sterilization. Ethylene oxide is toxic and carcinogenic to humans, so this permeation in turn requires an aeration period within the container of at least twelve hours. This process is considered time-inefficient, and, more importantly, because of the toxins employed and the air exchange required for complete aeration, dangerous.

Another such technique utilizes gamma radiation or electron beams with 5 to 10 Mev of energy. This technique, like the others, works as a batch process in that articles to be sterilized are put in a chamber of some type for some period of time. Both gamma-ray and electron beam devices are expensive due to the high cost of gamma sources and electron accelerators and the complexity of the safety system required for shielding of the operator from radiation. Certain important medical instruments are adversely effected by repeated exposures. For example, latex rubber cures and loses flexibility, and catheters become brittle.

Plasma sterilization addresses many of the above concerns. Low heats are used, often less than 150 deg. F. The gaseous plasma is not toxic or carcinogenic. Sterilization can also be accomplished in a reasonably short time. Radioactive sources are not necessary and therefore monitoring and disposal of sources is not required. Expensive safety and shielding is not necessary.

Plasma sterilizers are well known commercial apparatuses. New plasma sterilization chamber designs have been the subject of patents (e.g., U.S. Pat. No. 5,393,490). These apparatuses and the latest designs suffer from certain commercially important deficiencies, however. Most such sterilizers do not generate a homogeneous plasma density throughout the chamber, resulting in relatively long batch exposure times to ensure acceptable sterilization. The plasma density is also low, further lengthening the times. These low densities and poor homogeneities often dictate the use of special sterilizing gases, peroxides, for example, in order to shorten the sterilization time. The use of such gases adds expense. Recent patented designs use radio frequency (RF) or very high frequency (VHF) discharges requiring generators of electromagnetic radiation, entailing expense and requiring protection of servicing personnel from electromagnetic radiation.

Plasma sterilizer designs can be divided into two groups:

1) Those in which the plasma is generated in a separate chamber or in a small part of the sterilizer volume and is spread by diffusion into the chamber containing the articles to be sterilized (e.g., U.S. Pat. Nos. 3,948,601, 5,115,166, 5,413,760, 4,818,488, 4,898,715, 4,931,261, 5,451,368). This design results in losses of both charged and chemically active neutral particles of the plasma to the elements of the device and reduction of the intensity of the ultraviolet radiation. This design also results in significant non-homogeneity of plasma density due to losses of charged particles onto chamber walls and onto the instruments to be sterilized. Some designs employ a screen to allow only electrically neutral plasma particles into the sterilizing chamber (e.g., U.S. Pat. No. 5,413,760) since, in the opinion of the authors, the sterilization is accomplished by only the electrically neutral plasma particles. Such screening results in substantial lengthening of the sterilization time;

2) Those in which the plasma is generated directly within the sterilization chamber (e.g., U.S. Pat. No. 4,643,876, 4,818,488, 5,200,146). The devices described use RF (radio frequency) or VHF (very high frequency) fields for the generation of the plasma. H-type discharge in a skin layer near quartz or pyrex chamber walls is described in U.S. Pat. No. 4,643,876. E-type discharge actuated between an electrode inside the chamber and the chamber walls is described in U.S. Pat. No. 4,818,488. Microwave resonators are described in U.S. Pat. No. 5,200,146. The disadvantages of these devices is that the plasma density and homogeneity are disrupted by the type and amount of articles in the sterilizer, making the time to full sterilization uncertain. There is also added cost and complexity with use of RF and VHF generators and the related circuitry. Further still, in the case of the H-discharge and microwave fields, additional heating of articles can occur.

Sterilizers employing direct current (DC) glow discharge at low pressure are described in Jap. Pat. Nos. 53-35715, 60-58662. In all cases the discharge is direct: the electrons emitted from the cathode are accelerated directly towards the anode. The articles to be sterilized are simply placed between the cathode and anode and, thus, in the path of the electrons. Electrons emitted from the cathode do not spend all their energy in ionization and excitation of the gas. In addition, the articles disturb the natural electron path and, therefore, the discharge glowing, causing longitudinal and radial non-homogeneity of the plasma. These systems exhibit low energetic efficiency due to low utilization of the energy of the electrons emitted from the cathode. As with the RF and VHF designs described above, the plasma density and uniformity of these DC-glow designs are sensitive to the amount and type of articles to be sterilized, leading to longer batch times to ensure complete sterilization.

SUMMARY OF THE INVENTION

The primary object of the present invention consists in providing a plasma sterilizing apparatus and method for sterilization of medical articles both effectively and quickly at temperatures of 40–65 deg. C.

Another object of the present invention consists in providing a sterilizing apparatus and method without the use of any toxic substances in the form of feed gases or surface residuals and without any dangerous emissions.

Another object of the present invention is the providing of a faster, more reliable, and more economical sterilizing apparatus.

Another object of the present invention is to permit adjustment of the chamber power density, pressure, and batch time to allow temperatures in the chamber to escalate up to 160 deg. C., thus enabling the same apparatus to perform effective sterilization of heat-resistant metallic surgical and dental instruments by complex influence of the plasma factors and heat.

The design responsible for this improved plasma sterilization method consists of a unique glow discharge method. This unique discharge is between the chamber walls, which serve as the discharge cathode, and the electrode, or anode, which is positioned in a recessed manner within a hole in the chamber. As a result of this geometry, the vast majority of electrons escaping the cathode do not reach the anode in a single, direct flight—as they do in conventional glow discharge—but oscillate within the chamber volume as they are reflected and repelled by the surrounding cathode. This oscillating electron path 15 is depicted in FIG. 1b. In the conventional glow discharge method the electrons, once emitted, are accelerated directly towards the anode. This electronic path 14 is depicted in FIG. 1a. In FIG. 1a, electron 10 leaves cathode 11 for anode 12 past wall 13. The oscillating fast electrons depicted in FIG. 1b, which collide with the sterilizing gas to form the plasma, fill the chamber volume with a more homogeneous plasma. Such a configuration uses energy much more efficiently because the electrons emitted from the cathode are much more likely to collide with gas molecules and thus generate the gas plasma. In the preferred embodiment, the ratio of the hole area to the internal surface area of the cathode walls does not exceed a certain ratio, in this way assuring the electrons will so oscillate without sensing the anode.

The discharge resulting from this configuration is uniquely high in plasma concentration and homogeneity. This results from the fact that the oscillating electrons fill the chamber evenly. Such even distribution of electronic energy means the resulting plasma density and concentration can be generated very efficiently and the resulting plasma density can be elevated to quite high levels. Furthermore, the plasma homogeneity is largely insensitive to the number and type of articles placed in the chamber to be sterilized because, unlike other known configurations, there is no preferred electron path that is obstructed to various extents by said articles. These plasma properties combine to produce faster, more energy efficient, more reliable sterilization more insensitive to usage conditions and in a shorter, more energy efficient, more commercially practical time.

FIG. 1(a) is a diagram summarizing the operating principle and the electron path used in most plasma sterilizing devices of the art.

FIG. 1(b) demonstrates an approach taken in the instant application, illustrating the use of the cathode chamber walls to repel electrons and increase the ionizing efficiency.

DETAILED DESCRIPTION OF THE PREFERRED EMBODIMENT(S)

One of the ways to create an effective and safe sterilizer, one which will allow sterilization to occur over a wide range of temperatures in a short time and without the use of toxic chemicals or dangerous radiation, is with a gas discharge plasma. Such plasma is formed by an electrical current flow through a gas and/or vapor. Such plasma consists of ions, electrons, and molecules and atoms in ground and excited states. This plasma is quasi-neutral. Transitions of the excited atoms and molecules from excited to ground states result in the emission of electromagnetic, and particularly ultraviolet, radiation. The sterilization is achieved through the complex action of these plasma components with the surface contaminants—proteins, bacteria—on the articles to be sterilized.

Figure 1A:
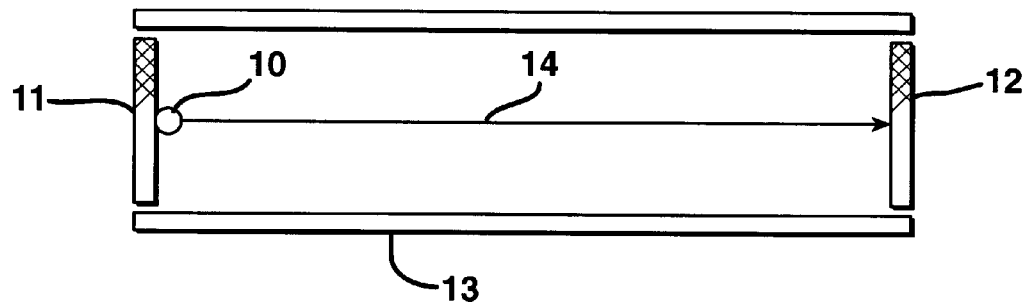
Figure 1B:
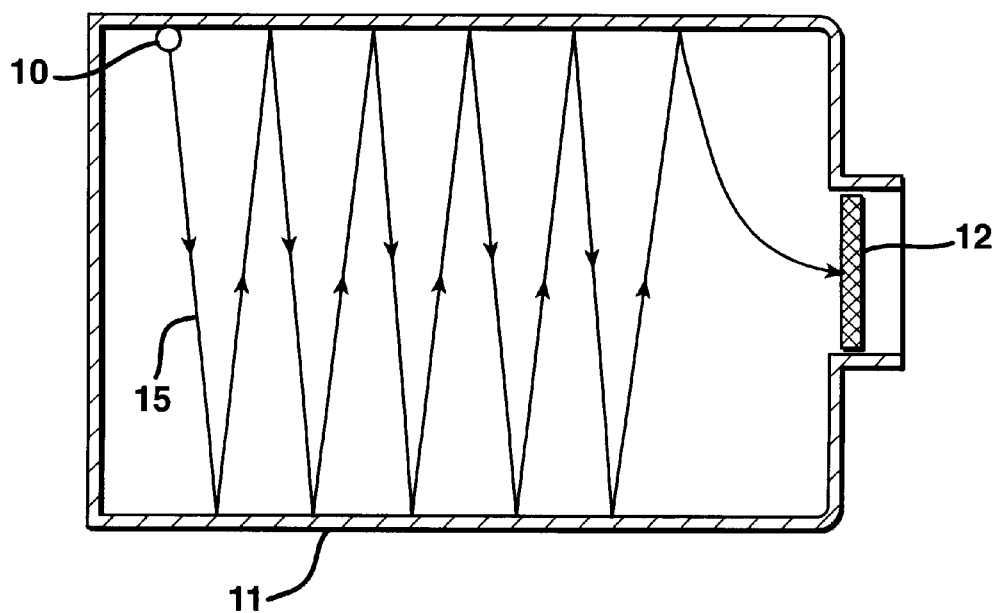
Figure 2:
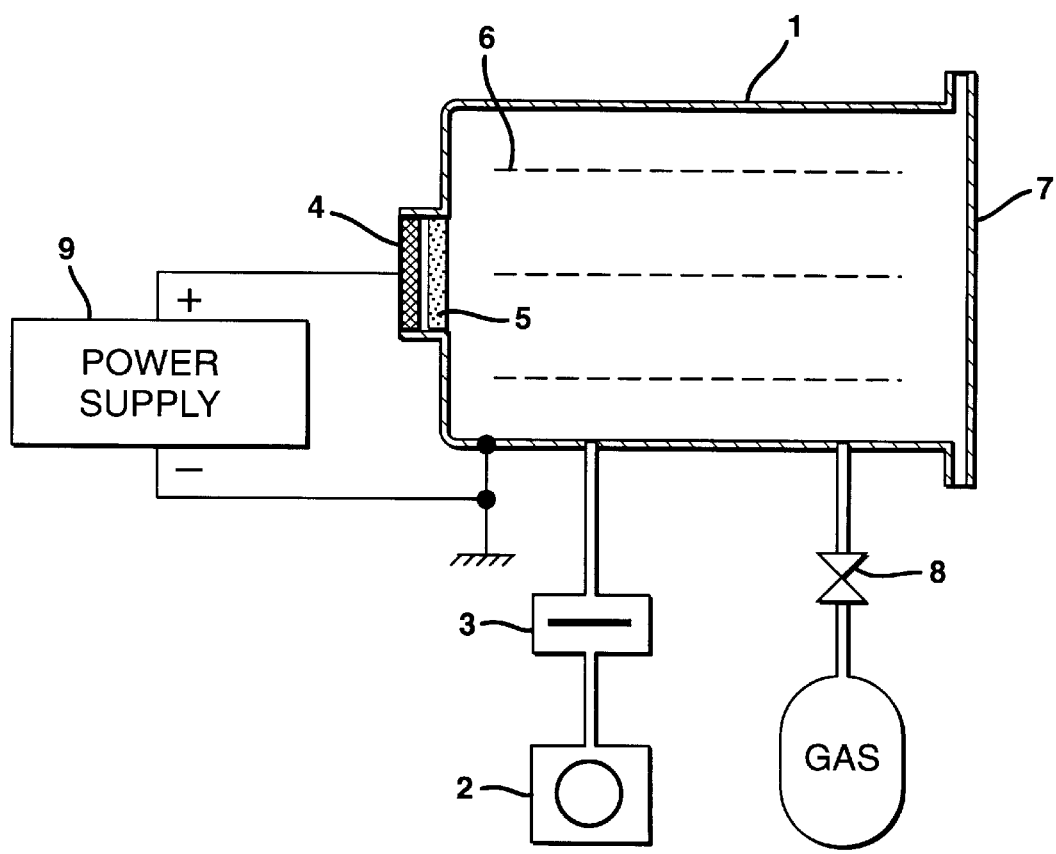
FIG. 2 is a detailed cross-sectional drawing of the invention showing the elements of the device.

FIG. 2 represents an embodiment of the suggested apparatus. The apparatus is comprised of a vacuum chamber 1, which is evacuated by the fore vacuum pump 2 through the oil trap 3. An isolator 4 is mounted in a hole of the chamber, and the anode 5 is attached to it. The facility 6 for placing of sterilized objects is mounted inside the vacuum chamber. The chamber has the hatch 7 for loading and unloading the sterilized articles. The feeding of plasma providing gas or vapor into the vacuum chamber is accomplished by means of gate 8. A positive pole of the power supply 9 is connected to the anode, whereas a negative one is attached to the walls of the vacuum chamber.

The device operates as follows. Articles to be sterilized are place in the vacuum chamber 1 on the facility 6 through the hatch 7. The vacuum chamber is evacuated by the pump 2 until the operating pressure is reached, the last being established by means of gate 8. The power supply is activated, providing a voltage between the vacuum chamber and anode 5. A glow discharge is thereby initiated in the chamber. Sterilization occurs as a result of the action of all the plasma components on the surface of the articles.

Tests were performed using such a plasma sterilizer with a cylindrical vacuum chamber 45 centimeters in length and 30 centimeters diameter. Stainless steel was used for the chamber walls. The hatch for loading the sterilized articles was situated at one end face of the chamber, whereas the anode was fastened to the other end face through the isolator. The chamber was evacuated by the forepump down to pressure of approximately 0.001 Torr, at which point the operating gas was introduced. Hydrogen, helium, argon, nitrogen, oxygen, or mixtures thereof, as well as air, were used as operating gas. Use of phenol (as in U.S. Pat. Nos. 4,207,286 and 4,348,357), and fluorine- and chlorine-containing gases was considered unreasonable because of the necessity for additional cleaning or deactivating of the surfaces of the sterilized articles of the toxic substances that could be formed in the plasma and deposited on the articles.

Figure 3:
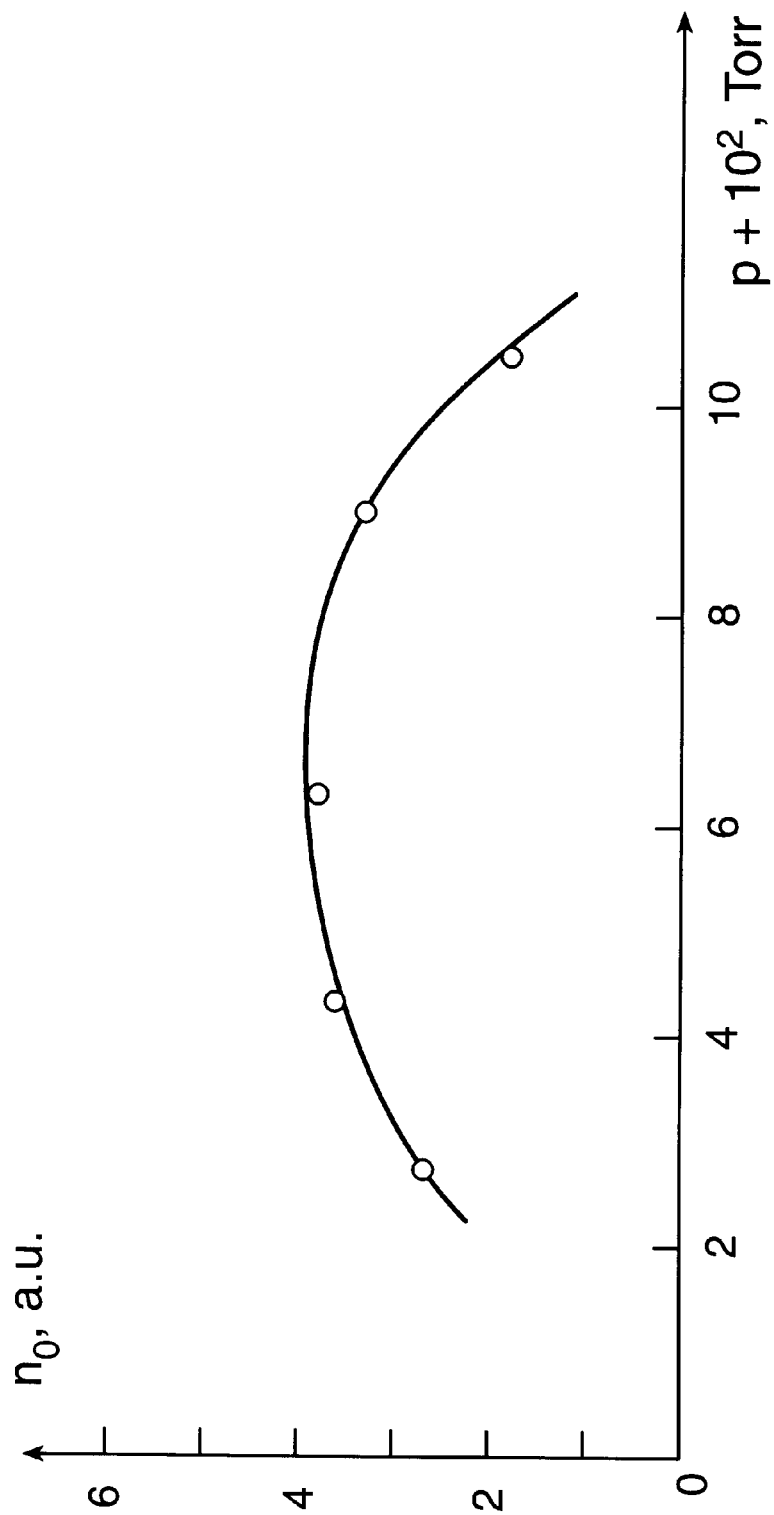
FIG. 3 illustrates how the operating principle illustrated in FIG. 1(b) and incorporated into the design in FIG. 2 results in a relatively insensitive response of the plasma density within the sterilization chamber to changes in the gas pressure within the chamber.

The plasma density in such a sterilizer depends on the type of gas and the specific power applied. Such power was adjusted in the range 0.001 to 0.05 Watts/cubic centimeter. The plasma concentration and degree of inhomogeneity were largely independent of gas pressure over a wide range of practical operating gas pressures. The use of air as the gas was studied to demonstrate this point, and plasma density was not strongly dependent on the gas pressure over the range 0.01 to 0.1 Torr (FIG. 3). The plasma density increases linearly with increasing power over the power range examined.

Figure 4:
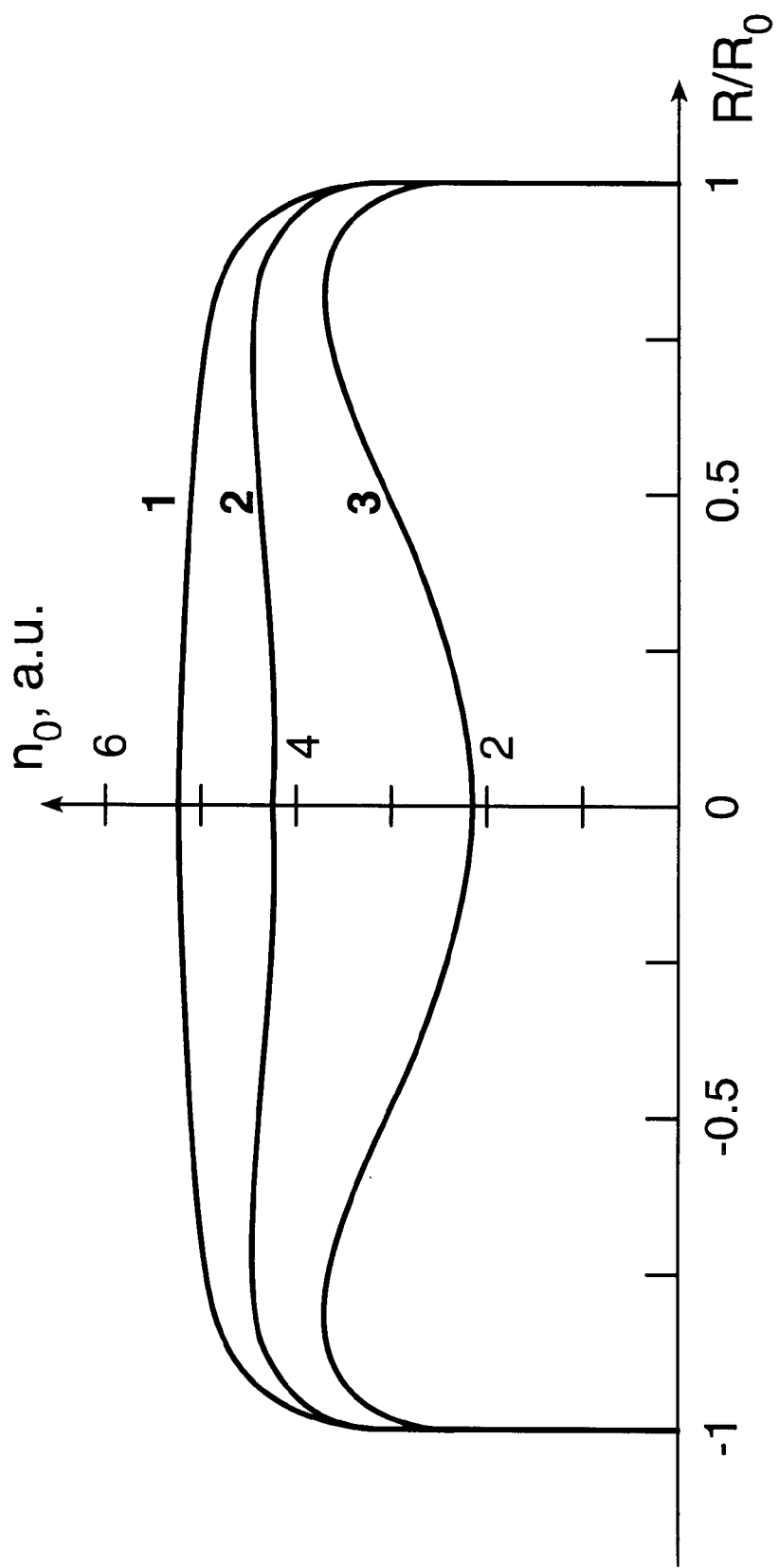
FIG. 4 illustrates the radial homogeneity of the plasma density over a series of specific gas pressures.

The distribution of plasma density along a radius of the vacuum chamber at a series of air pressures is presented in FIG. 4. The given curves show that radial inhomogeneity of the plasma does not exceed 25% over the range of gas pressure from 0.02 to 0.1 Torr.

Experiments have also been performed looking at various cross dimensions of the chamber a and gas pressure P, leading to a requirement for the product of the two variables, P * a. Similar experiments examined the area of the hole in which the anode is placed to the chamber wall area, $S_a/S_c$. The preferred range of the product P*a is 1 to 15 Torr*centimeters, most preferred 1.5 to 3 Torr*centimeters. The ratio of the hole area to the chamber wall area necessary to glean the benefits of the invention must be less than 0.25, but the optimum ratio depends on the gas pressure. With the gas pressure in the range 0.05- to 0.5-Torr, the most preferred range of the ratio $S_a/S_c$ is 0.005 to 0.1.

The superiority of this improved sterilizer design can be demonstrated using specific examples of operating parameters that result in faster, highly effective sterilization. For each of the following examples, a cylindrical chamber 30 centimeters in diameter and 45 centimeters in length served as the cathode, and the anode was positioned in a recessed area such that the ratio $S_a/S_c$ was 0.005.

The procedure in each of the following examples involved placing a Petri dish, on which spores of Bacillus subtilles had been deposited uniformly with predefined density, inside the sterilizing chamber. B. subtillis was used because it is thought to be the strain most resistant to the plasma action. Corresponding surface density of the spores was recorded. After sterilization the processed microorganisms are seeded by placing the processed instrument into a vital liquid: Hottingen sugar bouillon, tioglicole substance, Saburo bouillon. This liquid is then stored for 14 days at constant temperature: 37 deg. C. for Hottingen bouillon and tioglicole substance, 20–22 deg. C. for Saburo bouillon. Simultaneously the test is performed for infected Petri dishes which had not been processed in the sterilizer. After storage the visual test for the presence of grown colonies of bacteria is performed. Presence of only one colony for the sterilized articles means that sterilization failed. Thus only two results are recorded: "Test is successful—Total kill" or "Test failed." Results given in the following examples correspond to parameters of power density, gas pressure, type of gas and sterilization times which are thought to be in excess of that required for a successful result.

EXAMPLE 1

Spore density: $10^8$ spores/square centimeter (spores/cm$^2$)
Gas: Argon
Flowrate: 3 cubic centimeters/min (cc/min)
Pressure: 0.07 Torr
Power Density: 0.012 Watts/cubic centimeter (W/cc)
Exposure time: 12 minutes
Temperature: <60 degrees Celsius
Result: Total kill

EXAMPLE 2

Spore Density: $10^8$ spores/cm$^2$
Gas: Argon
Flowrate: 3.2 cc/min
Pressure: 0.08 Torr
Power Density: 0.015 W/cc
Exposure Time: 8 min
Temperature: <60 deg. C.
Result: Total kill

EXAMPLE 3

Spore Density: $10^6$ spores/cm$^2$
Gas: Air
Flowrate: 4.5 cc/min
Pressure: 0.1 Torr
Power Density: 0.016 W/cc
Exposure Time: 10 min
Temperature: 62 C.
Result: Total kill

EXAMPLE 4

Spore Density: $10^6$ spores/cm$^2$
Gas: Air
Flowrate: 4.5 cc/min
Pressure: 0.1 Torr
Power Density: 0.008 W/cc
Exposure Time: 15 min
Temperature: 46 C.
Result: Total kill

EXAMPLE 5

Spore Density: $10^5$ spores/cm$^2$
Gas: Air
Flowrate: 4.5 cc/min
Pressure: 0.1 Torr
Power Density: 0.025 W/cc
Exposure Time: 5 min
Temperature: 47 C.
Result: Total kill

EXAMPLE 6

Spore Density: $10^5$ spores/cm$^2$
Gas: Air
Flowrate: 4.5 cc/min
Pressure: 0.1 Torr
Power Density: 0.009 W/cc
Exposure Time: 15 min
Temperature: 59 C.
Result: Total kill

EXAMPLE 7

Spore Density: $10^5$ spores/cm$^2$
Gas: Oxygen (70%) and Nitrogen (30%)
Flowrate: 4.6 cc/min
Pressure: 0.1 Torr
Power Density: 0.016 W/cc
Exposure Time: 4 min
Temperature: 39 C.
Result: Total kill

EXAMPLE 8

Spore Density: $10^5$ spores/cm$^2$
Gas: Oxygen (70%) and Nitrogen (30%)
Flowrate: 4.5 cc/min
Pressure: 0.1 Torr
Power Density: 0.01 W/cc
Exposure Time: 7 min
Temperature: 41 C.
Result: Total kill These sterilization times are shorter, and therefore commercially superior, to other patented and commercially available plasma sterilizer apparatuses. Further, these shorter times are achieved using lower temperatures, less energy, and less dangerous gases than other commercial or patented sterilizers.

This same sterilizer apparatus can be used for doing dry heat sterilization. Cold plasma sterilization might appear ineffective when sterilizing metallic articles containing very narrow and long holes or where strong impurities are present on the instrument surface. Heating of metallic instruments up to 160 deg. C. is reached by decreasing the gas pressure to less than 0.1 Torr and increasing the power density applied to the discharge up to 0.1 Watts/cubic centimeter. Usage of such process for dry sterilization ensures such sterilization is accomplished in shorter time and with less power consumed than is used in conventional dry heat sterilization.

We claim:

1. Apparatus for sterilization of articles and materials in a gas plasma comprising:
   a gas-tight confined chamber having a metallic chamber wall connected to a point of potential reference;
   a metallic electrode which is placed in a hole of said chamber wall and is tightly mounted on said chamber wall by means of an isolator, with the ratio of the area of said hole to that of an internal wall surface of said chamber being not more than 0.25;
   means for applying positive potential to said electrode with respect to said point of potential reference;
   means for evacuating said chamber;
   means for flowing gas through said chamber; and
   means for placing said articles and materials within said chamber,
   wherein the apparatus is capable of sterilization of the articles and materials at temperatures of less than 65° C.

2. An apparatus for exposing an article at a temperature of less than 65° C. to a plasma comprising:
   a chamber defining a chamber surface exposed to a chamber volume;
   an electrode having a surface exposed to the chamber volume;
   means for flowing gas through said chamber;
   a power supply capable of generating a gas plasma in the chamber volume;
   an isolator which electrically insulates the electrode from the chamber.

3. The apparatus of claim 2 wherein the exposed electrode surface defines an electrode area, the exposed chamber surface defines a chamber wall area, and the ratio of the electrode area to the chamber wall area does not exceed 0.25.

4. The apparatus of claim 3 wherein the ratio of the electrode area to the chamber wall area does not exceed about 0.1.

5. The apparatus of claim 4 wherein the ratio of the electrode area to the chamber wall area is about 0.005 to about 0.10.

6. The apparatus of claim 5 further comprising a vacuum pump capable of reducing the pressure in the chamber to a pressure falling within the range of about 0.05 to about 0.5 Torr.

7. The apparatus of claim 2 wherein the isolator occupies a recessed portion of the chamber.

8. The apparatus of claim 7 wherein the electrode occupies the recessed portion of the chamber.

9. The apparatus of claim 8 wherein the chamber includes a chamber wall and the exposed electrode surface is substantially flush with a portion of the chamber wall.

10. The apparatus of claim 9 wherein the chamber wall includes a hatch.

11. The apparatus of claim 2 wherein the chamber is electrically connected to the power supply.

12. The apparatus of claim 11 wherein the chamber is a hollow cathode electrically connected to a negative pole of the power supply and the electrode is an anode electrode electrically connected to the positive pole of the power supply.

13. The apparatus of claim 11 wherein the chamber volume is substantially cylindrical in shape, and is defined by a diameter and a length.

14. The apparatus of claim 2 wherein the chamber has a cross dimension and further comprises a vacuum pump capable of establishing an operating pressure within the chamber such that the mathematical product of the pressure and the cross dimension is from about 1 to about 15 Torr-centimeters.

15. The apparatus of claim 14 wherein the mathematical product of the pressure and the cross dimension is about 1.5 to about 3.0 Torr-centimeters.

16. The apparatus of claim 2 wherein the power supply is capable of producing a power density in the chamber of about 0.001 to about 0.05 W/cm$^3$.

17. A gas plasma sterilization apparatus capable of sterilization of articles and materials at temperatures of less than 65° C. comprising:
   an anode electrode;
   a vacuum chamber defined by a cathode chamber wall having a recessed portion within which the anode electrode is positioned;
   an electrical insulator between the cathode chamber wall and the anode electrode;
   a hatch portion of the chamber wall;
   a gas inlet for the vacuum chamber;
   a vacuum pump for the vacuum chamber; and
   a direct current power supply including a positive pole electrically connected to the anode and a negative pole electrically connected to the chamber wall.

18. The apparatus of claim 17 wherein the chamber is substantially cylindrical in shape, the anode electrode and hatch portion are positioned at opposite ends of the chamber, and the vacuum pump is capable of reducing chamber pressure such that the mathematical product of the chamber pressure and diameter of the chamber falls within the range of about 1 to about 15 Torr-centimeters.

19. The apparatus of claim 17 wherein a power density within the chamber provided by the power supply is about 0.001 to about 0.05 W/cm$^3$.

20. The apparatus of claim 17 wherein a ratio of the area of the anode electrode exposed to the chamber volume to an area of the chamber wall is 0.25 or less.

21. A process for sterilizing an article comprising:
   placing the article within an apparatus comprising an anode electrode in a vacuum chamber defining a chamber wall cathode;
   reducing pressure in the chamber to below atmospheric pressure;
   introducing into the chamber an operating gas selected from the group consisting of hydrogen, helium, argon, nitrogen, oxygen, air, hydrogen peroxide, peracetic acid, and mixtures thereof;
   supplying electrical power to the chamber wall cathode and the anode to initiate a glow discharge and a power density within the chamber of about 0.001 to about 0.05 W/cm$^3$; and exposing said article to said glow discharge at a temperature of less than 65° C., thereby sterilizing said article.

* * * * *